United States Patent [19]

Molnar et al.

[11] Patent Number: 4,532,249
[45] Date of Patent: Jul. 30, 1985

[54] DERIVATIVES OF P-ACYLAMINOPHENOL HAVING A THERAPEUTIC ACTION, AND COMPOSITIONS HAVING A THERAPEUTIC ACTION CONTAINING SAID DERIVATIVES AS PHARMACOLOGICALLY ACTIVE INGREDIENTS

[76] Inventors: Francois Molnar, Chalet Pilouhé1936 Verbier; Suzanne Szabo, Avenue de Sully, 1, 1814 La Tour-de-Peilz; Peter R. Statkov, 6 rue du Roveray, 1207 Geneva, all of Switzerland; Manuel Armijo, Mateo Inurria 30, Madrid 16, Spain; Carlos Sunkel, Mateo Inurria 30, Madrid 16, Spain; Fernando Cillero, Mateo Inurria 30, Madrid 16, Spain

[21] Appl. No.: 437,318

[22] Filed: Oct. 28, 1982

[30] Foreign Application Priority Data

Nov. 2, 1981 [CH] Switzerland .......................... 7000/81
Apr. 26, 1982 [CH] Switzerland .......................... 2507/82

[51] Int. Cl.³ .................. C07D 295/12; C07D 295/14; A61K 31/535

[52] U.S. Cl. .................................... 514/324; 544/144; 544/165; 546/201; 546/232; 548/467; 548/500; 548/568; 560/38; 560/39; 560/43; 564/170; 514/331; 514/428; 514/534; 514/621; 514/419

[58] Field of Search ................. 544/144, 165; 546/201, 546/232; 548/467, 500, 568; 560/38, 39, 43; 564/170; 424/248.54, 267, 274, 309, 324

[56] References Cited

U.S. PATENT DOCUMENTS 3,729,470  4/1973  Vaille ................................... 548/568

FOREIGN PATENT DOCUMENTS 940828  3/1956  Fed. Rep. of Germany ...... 564/110

OTHER PUBLICATIONS

Noller, "Chemistry of Organic Compounds" 2nd Ed. (1957), p. 504 (Saunders).

Primary Examiner—Robert T. Bond
Attorney, Agent, or Firm—Pennie & Edmonds

[57] ABSTRACT

New acyl derivatives of p-aminophenol and esters of same useful as pharmacologically active ingredients and process for their preparation.

4 Claims, No Drawings

DERIVATIVES OF P-ACYLAMINOPHENOL HAVING A THERAPEUTIC ACTION, AND COMPOSITIONS HAVING A THERAPEUTIC ACTION CONTAINING SAID DERIVATIVES AS PHARMACOLOGICALLY ACTIVE INGREDIENTS

SUMMARY OF THE INVENTION

The invention relates to new and useful derivatives of p-acylaminophenol having the formula

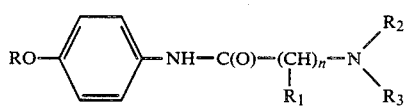

in which R represents a hydrogen atom or an acyl radical derived from an organic acid chosen from the following acids: acetylsalicylic, 5-(2,4-difluorophenyl)-acetylsalicylic, 1-(p-chlorobenzoyl)-5-methoxyindolylacetic, 1-(4-chlorobenzoyl)-5-methoxy-2-methyl-3-indolylacetic, 2-(p-isobutylphenyl)-propionic, d-2(6-methoxy-2-naphtyl)-propionic acid, 2-(3-benzoyl-phenyl)-propionic acid, and 2-(2,3-dimethyl-phenylamino)-benzoic acid and 2-(3-tri-fluoromethyl-phenyl phenylamino)-benzoic acid; wherein n is equal to zero, 1, 2 or 3;

$R_1$ represents a hydrogen atom or a methyl group;

$R_2$ and $R_3$, which may be identical or different, each represent a linear or branched alkyl group, containing 1 to 4 carbon atoms, 2-hydroxyethyl or 2,3-dihydroxypropyl; or in which the radical

may form a heterocycle such as morpholyl, piperidyl, pyrrolidyl for example and their salts with pharmaceutically acceptable acids.

The invention also relates to a process for preparing said derivatives, as well as to pharmaceutical compositions containing at least one of the compounds defined above as pharmacologically active ingredient.

BACKGROUND OF THE INVENTION

N-acetyl-p-aminophenol has proved beneficial in medical practice due to its analgesic action. However, this compound is not exempt from certain toxic effects in high doses, in particular hepatotoxicity.

Certain compounds resulting from the combination of p-aminophenol and various amino acids, in particular compounds having the formula I in which the symbol R represents a hydrogen atom, have been found to possess useful analgesic properties in therapeutic doses. They alleviate various types of pain. The most active representatives of these new products possess qualities superior to those of the reference product (N-acetyl-p-aminophenol): they are less toxic and the difference between therapeutic doses and those which provoke undesirable side effects is greater; in addition, they are highly soluble in water and may be used in injectable galenic forms, which is not the case for N-acetyl-p-aminophenol.

Furthermore, it is well known that certain organic acids such as acetylsalicylic acid, 5-(2,4-difluorophenyl)-acetylsalicylic acid, 1-(p-chlorobenzol)-5-methoxyindoleacetic acid, certain arylpropionic acids and certain anilinophenylcarboxylic or acetic acids are used in human medicine as non-steroidal anti-inflammatory agents and analgesics.

Nevertheless, the use of these acids is generally accompanied by various types of gastro-intestinal disorder, inparticular hemorrhages and ulcers.

Surprisingly, it has been found that compounds of formula I in which the symbol R represents an acyl radical derived from organic acids such as those defined hereinabove are highly active biological compounds and that, in comparison with the parent acids, the most interesting members of the series are appreciably less toxic, less harmful and less ulcerigenic, while still possessing remarkable efficacy and a more favourable therapeutic index.

PREFERRED EMBODIMENTS OF THE INVENTION

The invention therefore relates to compounds of formula I as defined in claim 1 as well as to the salts they form with pharmacologically acceptable mineral or organic acids.

Compounds of formula I in which the symbol R represents a hydrogen atom may be prepared from p-haloacylaminophenols having the formula II. Said compounds II are described (Beilstein 13, 160), while secondary amines having the formula III are commercially available products; we used them in a chemically pure form for the following tests.

One embodiment of the procedure consists in slowly adding the compound having the formula II dissolved in an anhydrous solvent to the solution of the secondary amine of formula III - at a suitable temperature - and then filtering the salts, evaporating the solvent, and precipitating the base by adding a solvent such as ethyl acetate or diisopropyl ether.

The secondary amine may also be used advantageously as an acid acceptor, i.e. an excess of 100–130%. If the salt of the secondary amine is soluble in the solvent as used, a tertiary amine such as triethylamine or pyridine is used as the acid acceptor.

A highly recommended embodiment consists in carrying out the said reaction in dry methylformamide or anhydrous methyl ethyl ketone.

A favourable temperature range for carrying out the said reaction is 20°–100° C. The duration of the reaction may vary from 2 hours to 5 days.

One embodiment for isolating the compound formed consists in filtering the salts, evaporating the solvent and excess amine under vacuum, and then precipitating the base by adding a suitable solvent such as ethyl acetate or diisopropyl ether.

Another method of isolating the compound consists in treating the residue on evaporation in a solvent such as isopropanol, ethyl acetate or acetone with an acid dissolved in an alcohol, or in the gaseous state, so as to precipitate the required salt.

The phenolic compounds so obtained may then be converted into the corresponding esters according to the procedure of the invention, by reaction with the haloids of the above-mentioned organic acids. The chlorides of these acids, in particular, are known and readily available.

One embodiment of the procedure consists in reacting a phenol of formula IV (R=H) with a corresponding acid chloride in the presence of a tertiary base in a suitable solvent, at adequate temperatures, then washing the reaction mixture to neutrality with water, drying and evaporating the organic phase, and finally recrystallizing the raw product obtained.

According to the invention, the reactants are used in equimolecular quantities or in 10-15% excess for certain acid chlorides. A tertiary base may be used advantageously as an acid acceptor, for example triethylamine or pyridine.

According to one particularly advantageous embodiment, suitable quantities of the compounds are reacted in an organic solvent, for example methylene chloride, chloroform or dry toluene. A favourable temperature range for carrying out the said procedure is 10°-110° C. The duration of the reaction may vary from 2 to 24 h.

The new compounds having the formula I form salts with acidic substances. These salts may be obtained by treating the residue on evaporation in a solvent such as isopropanol, acetone or ether with an acid dissolved in an alcohol, or in the gaseous state, so as to precipitate the required salt.

A highly recommended embodiment for obtaining the said salts consists in reacting an acid chloride and the salt of dialkylaminoacetamidophenol of formula IV (R=H) in the presence of a tertiary base, using them in approximately equimolecular quantities. In this way, the required salt in obtained directly and may be purified by recrystallization.

As stated previously, certain compounds of formula I exert the analgesic effect, whereas others are both analgesic and anti-inflammatory.

Examples of compounds having an analgesic action are phenolic compounds of formula I (R=H) in which each of the symbols $R_2$ and $R_3$ represent a lower alkyl radical: p-N,N-diethylglycylamidophenol and its hydrochloride have proved highly effective. Strong analgesic effects have been demonstrated using doses between approximately 100 and approximately 300 mg/kg during the acetylcholine test in mice (administration per os; $ED_{50}$ approximately 140 mg/kg).

Examples of compounds having an analgesic and an antiinflammatory action are the 1-(4-chlorobenzol)-5-methoxy-2-methyl-3-indolylacetate of 4-N,N-diethylaminoacetamidophenyl and its hydrochloride. The efficacy of the latter as an analgesic has been demonstrated using doses of approximately 0.5 to approximately 8 mg/kg during the phenylbenzoquinone test in mice ($ED_{50}$ approx. 2.3 mg/kg).

The said hydrochloride also exerts a strong anti-inflammatory action during the inhibition of plantar edema in the rat induced by carrageenin ($ED_{50}$ approx. 16.7 mg/kg). This compound also exerts an antiarthritic and an antipyretic action.

The desired therapeutic effect may be advantageously obtained by using compounds of formula I in combination with an excipient, a support or an ordinary inert diluant.

The following examples illustrate the present invention without in any way restricting its scope.

EXAMPLE 1

To a 77.5 g (1.06 mol) solution of diethylamine in 180 ml of anhydrous dimethylformamide is added, drop by drop, a 49.3 g (0.265 mol) solution of N-α-chloroacetyl-p-aminophenol in 80 ml of anhydrous dimethylformamide. This addition is carried out at a rate such that the temperature of the mixture does not exceed 30° C.; the mixture is then heated, while stirring, for 2 hours at a temperature between 45° and 50° C., and allowed to cool, the diethylamine hydrochloride formed is filtered and the solvent evaporated under vacuum. 450 ml of ethyl acetate is added to the residue (65.7 g) to precipitate a second fraction of diethylamine hydrochloride, which is then filtered, and the mother liquor is acidified with hydrochloric acid dissolved in isopropanol. In this way, 50.4 g of p-N,N-diethylglycylamidophenol are obtained, which melt at 204°-206° C. By evaporating the acidic mother liquor, 17.4 g of the product may be recovered, which after recrystallization in 150 ml of absolute ethanol gives 8.6 g of the hydrochloride; MP 204°-206° C. The yield for both fractions is 86%.

Example 2

A solution of 9.3 g (0.05 mol) of N-α-chloroacetyl-p-aminophenol in 50 ml of anhydrous methyl ethyl ketone is added to a solution of 5.3 g (0.05 mol) of diethanolamine and 7 ml (0.05 mol) of triethylamine in 20 ml of anhydrous methyl ethyl ketone, and then heated for 10 hours under reflux. After cooling, the triethylamine hydrochloride is filtered and the ketone evaporated under vacuum. The residue (18.7 g) is taken up in 150 ml of acetone, treated with carbon and then acidified with a solution of hydrochloric acid in isopropanol to obtain p-N,N-di-(β-hydroxyethyl)-glycylamidophenol; MP 141°-142° C.

EXAMPLE 3

By following the methods described in examples 1 and 2 above, one may obtain:

p-N,N-dimethylglycylamidophenol.HCl; MP 227°-229° C.

p-N,N-diisopropylglycylamidophenol. HCl; MP 238°-242° C.

p-N,N-diethyl-α-alanylamidophenol.HCl; MP 196°-197° C.

p-N,N-dibutylglycylamidophenol.HCl; MP 121°-122° C.

1-N-morpholino-p-acetamidophenol.HCl; MP 183°-184° C.

p-N,N-dipropylglycylamidophenol.HCl; MP 195°-196° C.

p-N-ethyl-N-isopropylglycylamidophenol.HCl; MP 204°-205° C.

p-N-(β-hydroxyethyl)-N-isopropylglycylamidophenol.HCl; MP 168°-169° C.

p-N-(2,3-dihydroxypropyl)-N-isopropylglycylamidophenol maleate; MP 159°-160° C.

1-N-piperidino-p-acetamidophenol.HCl; MP 217°-218° C.

EXAMPLE 4

7.4 g (0.037 mol) of acetylsalicyloyl chloride is added to a solution of 7.6 g (0.034 mol) of 4-N,N-diethylaminoacetamidophenol and 4.05 g (0.04 mol) of triethylamine in 40 ml of dry toluene in such a way that the temperature of the mixture does not exceed 50° C. When addition is complete, the mixture is heated for 6 hours under reflux. After cooling, it is poured onto 50 ml of $H_2O$, the layers are allowed to separate, the organic layer is washed to neutrality, dried over $Na_2SO_4$ and the solvent eliminated under vacuum. On recrystallization of the residue (13 g) in 240 ml of isopropyl ether, 9.1 g of 4-N,N-diethylaminoacetamidophenyl acetylsalicylate are obtained; MP 99°-100° C., with a yield of 69.6%. The hydrochloride of this base melts at 117°–118° C.

4-N,N-diethylaminoacetamidophenyl hydrochloride acetylsalicylate; MP 152°–157° C. (dec.) may be obtained by the method described above.

EXAMPLE 5

To a solution of 56.4 g (0.15 mol) of 1-(4-chlorobenzoyl)-5-methoxy-2-methyl-3-indolylacetyl chloride in 500 ml of dry chloroform and 21 ml (0.15 mol) of triethylamine, 38.8 g (0.15 mol) of 4-N,N-diethylaminoacetamidophenol.HCl are added, in portions. The mixture is stirred for 6 hours at ambient temperature, washed with a little water, the chloroform solution is dried over $Na_2SO_4$ and the solvent evaporated under reduced pressure. On recrystallization of the residue in isopropanol, 4-N,N-diethylaminoacetamidophenyl 1-(4-chlorobenzoyl)-5-methoxy-2-methyl-3-indolylacetate hydrochloride is obtained; MP 179°–180° C. (dec.), with a yield of 70%.

EXAMPLE 6

To a solution of 89.9 g (0.4 mol) of 2-(p-isobutylphenyl)propionyl chloride in 300 ml of dry methylene chloride are added 103.2 g of 4-N,N-diethylaminoacetamidophenol.HCl (0.4 mol) and then 56 ml (0.4 ml) of triethylamine. The mixture is heated for 2 hours under reflux, allowed to cool, washed with water, dried over anhydrous $Na_2SO_4$ and then evaporated under vacuum. The solid residue is recrystallized in isopropanol; in this way one obtains 4-N,N-diethylaminoacetamidophenyl 2-(p-isobutylphenyl)-propionate as the hydrochloride with a yield of 80%; MP 153°–155° C.

4-N,N-diisopropylaminoacetamidophenyl hydrochloride 2-(p-isobutylphenyl)-propionate may be obtained by the method described above; MP 140°–143° C. (dec.).

What we claim is:

1. A compound having the formula

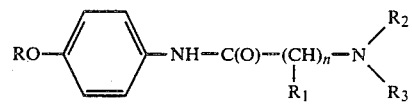

in which R represents an acyl radical derived from an organic acid chosen from the following acids: 1,(4-chlorobenzoyl)-5-methoxy-2-methyl-3-indolylacetic, and 2-(p-isobutylphenyl)-propionic, wherein n is equal to 1;

$R_1$ represents a hydrogen atom or a methyl group;

$R_2$ and $R_3$, are identical, each represents an ethyl group, and their salts with pharmaceutically acceptable acids.

2. Composition having a therapeutic action, characterized in that it contains, as a pharmacologically active ingredient an analgesic antiinflammatory, antiarthritic and antipyretic, compound of Formula I as defined in claim 1 and an effective amount of a carrier, excipient or inert diluent.

3. Composition having an analgesic and/or antiinflammatory action, characterized in that it contains, as a pharmacologically active ingredient, a compound of Formula I as defined in claim 1, and an effective amount of a carrier, excipient or inert diluent.

4. The compound p-N,N diethylglylamidophenol and an effective amount of its hydrochloride and an effective amount of a carrier, excipient or inert diluent as an analgesic.

* * * * *

UNITED STATES PATENT AND TRADEMARK OFFICE
CERTIFICATE OF CORRECTION

PATENT NO. : 4,532,249

DATED : July 30, 1985

INVENTOR(S) : Francois Molnar et al

It is certified that error appears in the above-identified patent and that said Letters Patent is hereby corrected as shown below:

Column 6, line 32, "p-N,N diethylglylamidophenol" should read "p-N,N-diethylglycylamidophenol"

Signed and Sealed this

Eleventh Day of February 1986

[SEAL]

Attest:

DONALD J. QUIGG

Attesting Officer

Commissioner of Patents and Trademarks